(12) United States Patent
King

(10) Patent No.: US 6,503,229 B2
(45) Date of Patent: Jan. 7, 2003

(54) NEEDLE RECEPTACLE

(76) Inventor: Morris T. King, 530 Central Ct., Indianapolis, IN (US) 46205

( * ) Notice: Subject to any disclaimer, the term of this patent is extended or adjusted under 35 U.S.C. 154(b) by 34 days.

(21) Appl. No.: 09/810,719

(22) Filed: Mar. 16, 2001

(65) Prior Publication Data

US 2002/0133125 A1 Sep. 19, 2002

(51) Int. Cl.$^7$ .......................... A61M 5/00; A61M 5/32; A61M 5/178; A61M 25/16; A61M 25/18
(52) U.S. Cl. .................. 604/263; 604/110; 604/162; 604/164.08; 604/171; 604/197; 604/198; 604/174; 604/539
(58) Field of Search ................................ 604/110, 162, 604/164.08, 171, 197, 198, 263, 539, 174; 128/DIG. 26, DIG. 6

(56) References Cited

U.S. PATENT DOCUMENTS

| | | | |
|---|---|---|---|
| 4,559,042 A | * 12/1985 | Votel | 604/192 |
| 4,927,415 A | 5/1990 | Brodsky | |
| 5,267,975 A | * 12/1993 | Brodsky | 604/198 |
| 5,282,479 A | 2/1994 | Havran | |
| 5,423,756 A | * 6/1995 | van der Merwe | 605/110 |
| 5,562,636 A | 10/1996 | Utterberg | |
| 5,704,924 A | 1/1998 | Utterberg | |
| 5,772,638 A | 6/1998 | Utterberg | |
| 5,951,529 A | 9/1999 | Utterberg | |
| 6,165,157 A | 12/2000 | Jagmohanbir | |

* cited by examiner

Primary Examiner—Timothy L. Maust
Assistant Examiner—Anuradha Ramana
(74) Attorney, Agent, or Firm—Michael A. Myers; Bingham McHale LLP

(57) ABSTRACT

A needle receptacle is provided for use with needle assemblies typically used in blood banks. The needle assemblies of the type concerned here have a needle mount with a forward end and a rearward end, a needle extending from the forward end of the needle mount and a flexible tube extending from the rearward end of the needle mount that connects the needle assembly in fluid-flow connection with a blood collection bag. The needle receptacle has an elongated hollow body with a front end and a rear end. The front end is open and sufficiently sized to permit the needle mount to pass axially through it. The rear end has a bore formed in it. The bore is sufficiently sized to permit the tube to pass axially through it, but too small to permit passage of the needle mount. There is also an opening formed in the body between the front end and the rear end for receiving the needle mount and the needle so that the hollow body can be slidably mounted onto the needle assembly.

14 Claims, 3 Drawing Sheets

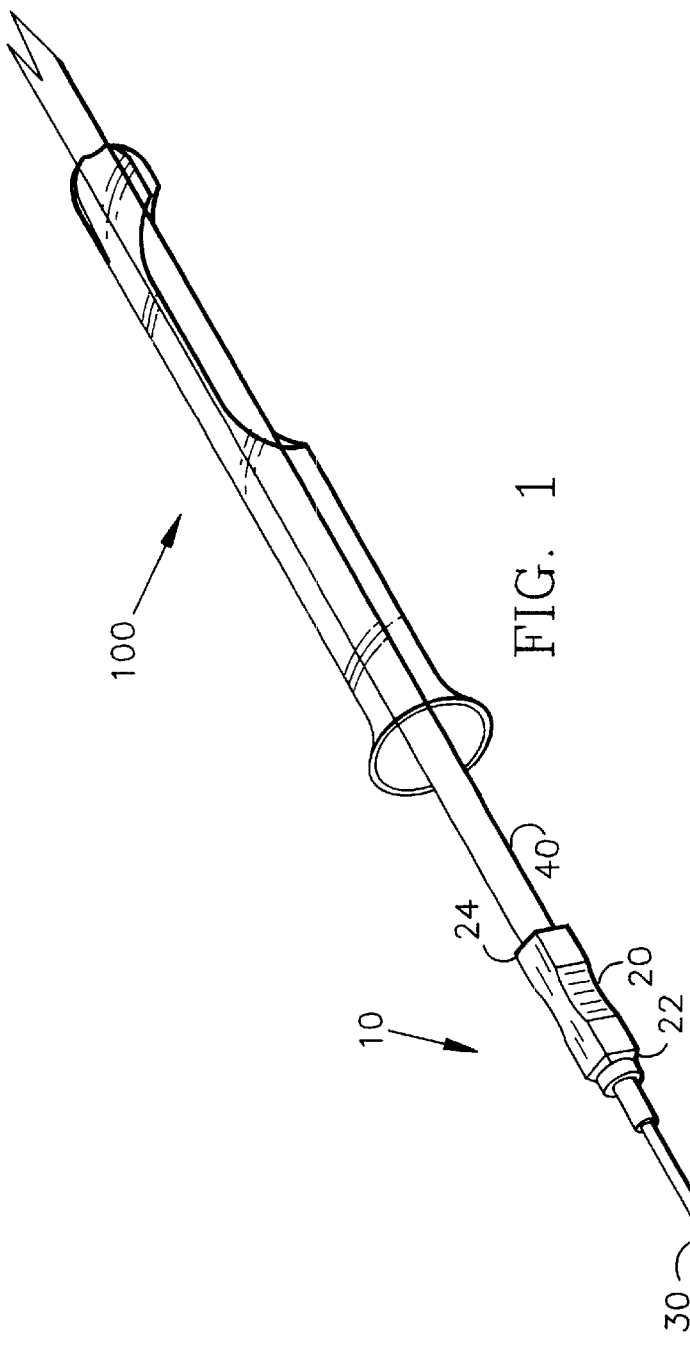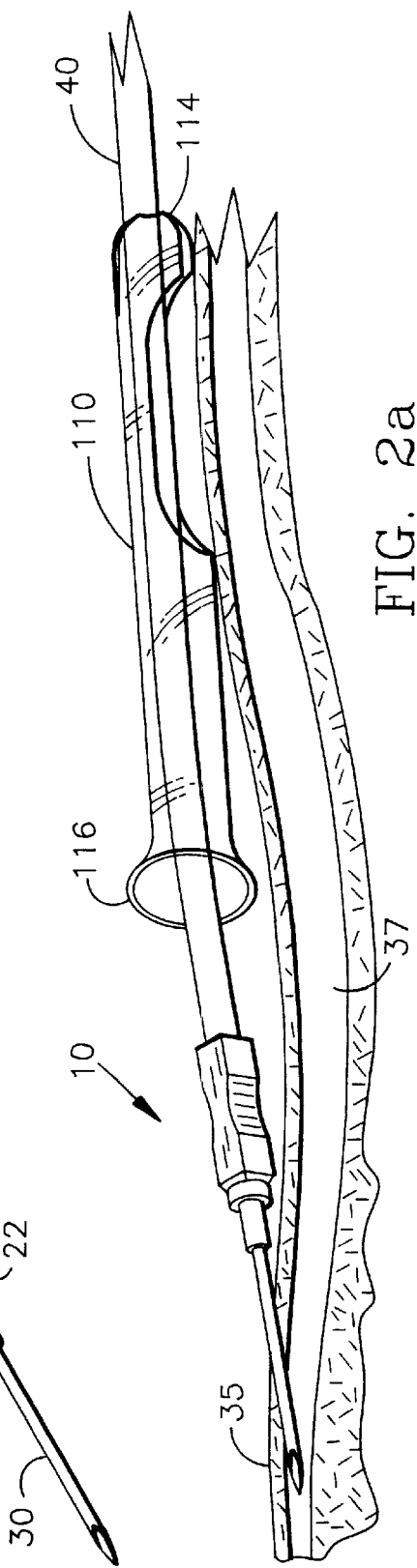

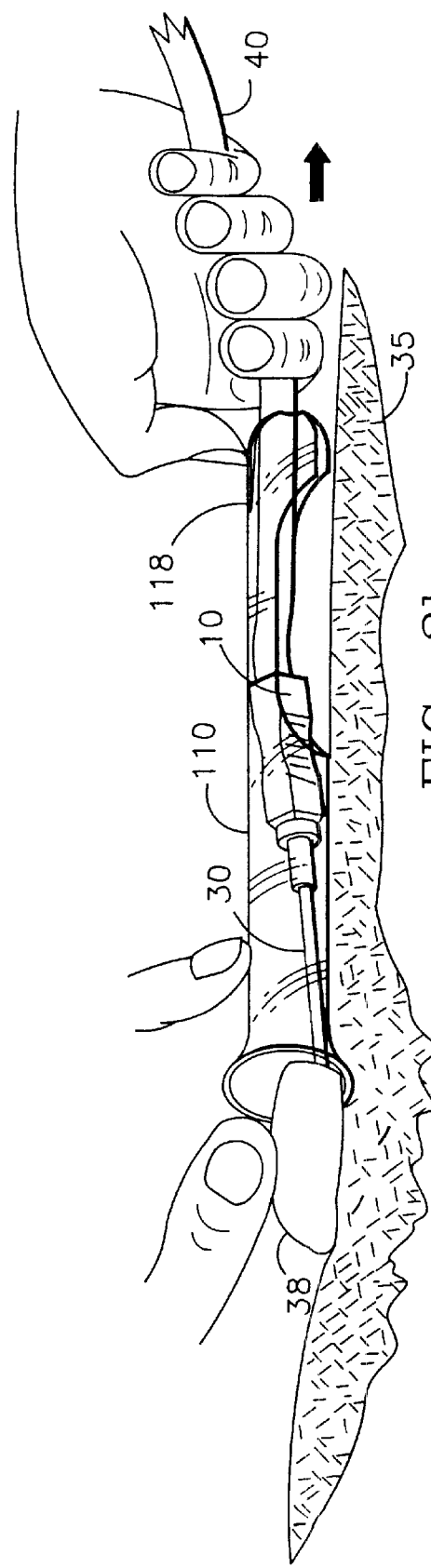
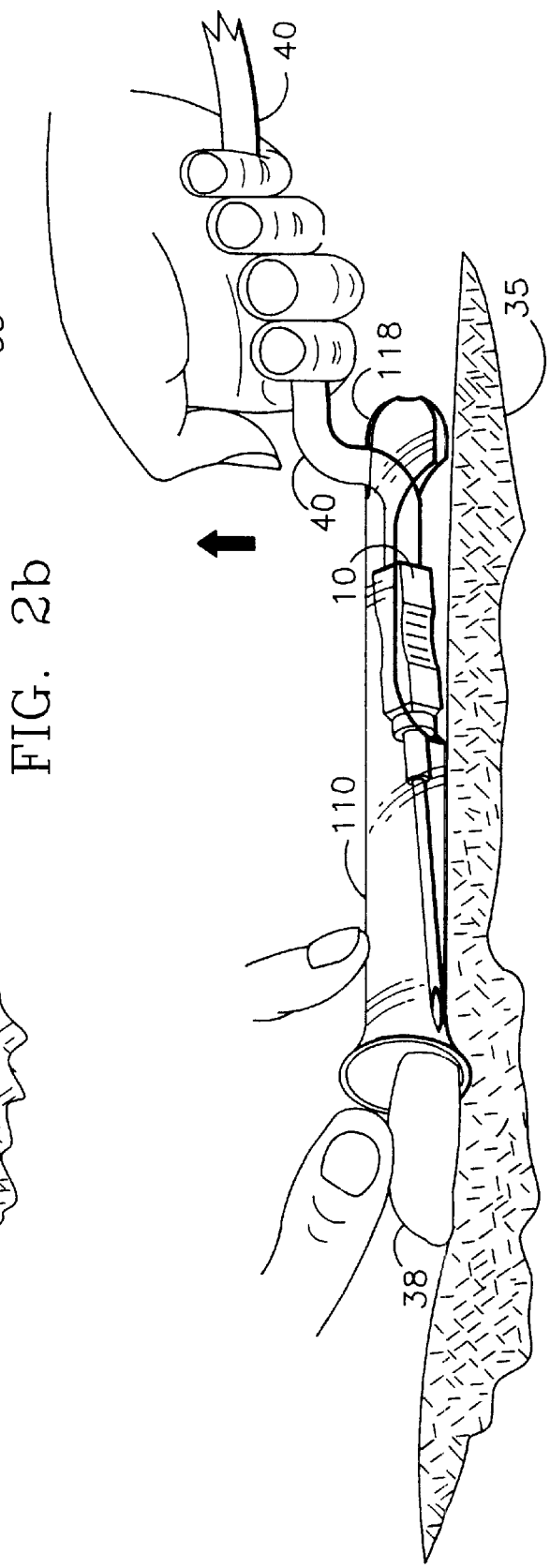

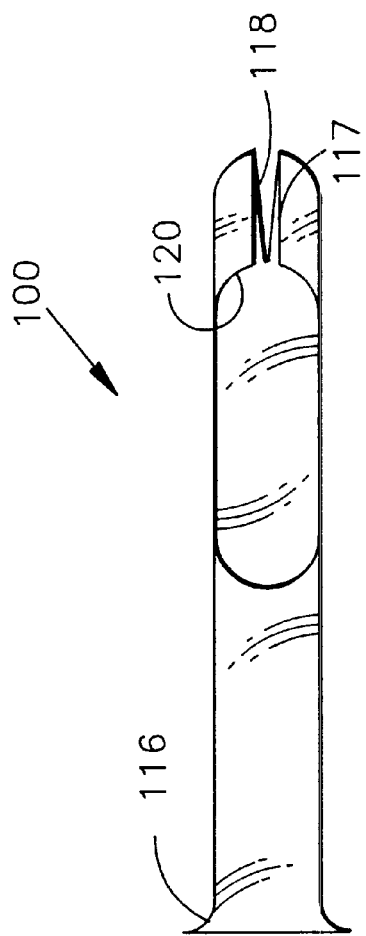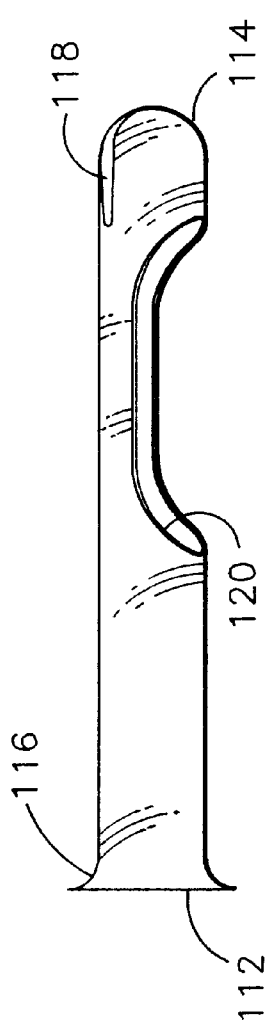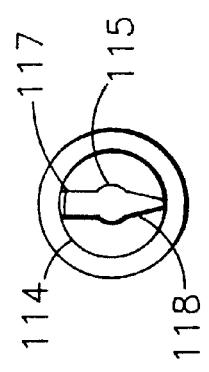

NEEDLE RECEPTACLE

BACKGROUND

The present invention pertains to protective devices for protecting against needle-stick injuries by a medical catheter or needle. More particularly, the invention pertains to a needle receptacle for use with needle assemblies of the type used by blood banks.

Needle sticks and other percutaneous injuries resulting in exposure to blood and other potentially infectious materials continue to be of concern due to the high frequency of their occurrence and the severity of the health effects associated with exposure. At the time of this writing, the Center for Disease Control and Prevention has estimated that healthcare workers in hospital settings sustain 384,325 percutaneous injuries involving contaminated "sharps" annually. When non-hospital healthcare workers are included, the best estimate of the number of percutaneous injuries involving contaminated sharps is nearly 600,000 per year.

When these injuries involve exposure to infectious agents (e.g., human immunodeficiency virus (HIV), hepatitis B virus (HBV), and hepatitis C virus (HCV)), the affected workers are at risk for contracting disease. Workers may also suffer from adverse side effects of drugs used for post-exposure prophylaxis and from psychological stress due to the threat of infection following an exposure incident. Since publication of the Bloodborne Pathogens (BBP) standard, a wide variety of medical devices have been developed to reduce the risk of needle sticks and other sharps injuries.

U.S. Pat. No. 6,165,157 to Dillon et al. discloses a guard formed from plastic that has a top hingedly secured to the bottom. The guard is enclosed around the flexible tube of the needle assembly. Interlocking tabs hold the top and bottom of the guard together. The guard also has flexible protrusions extending into the guard's interior that prevent the needle mount portion of the needle assembly from being removed from the guard once the needle and mount are inside.

Though likely to help reduce needle-stick injury and/or contact with blood exuded from the needle ('blood-splash') during withdraw procedures, this device has several shortcomings. Its plastic hinge, flexible protrusions and tabs add to die cast manufacturing cost and can break during use as a result of stress forces. Another problem with the Dillon device is that it cannot be used with all bloodpack needle assemblies. Some manufacturer's needle mounts do not fit between the top and bottom of Dillon's device once the interlocking tabs are secured together. Coincidentally, the openings defined at both ends of the guard are not sufficiently sized to receive the needle mount of some manufacturers. Therefore, it is highly desirable to provide a new needle receptacle for use with needle assemblies of the type used by blood banks.

It is also highly desirable to provide a new needle receptacle that will reduce the number of needle sticks and percutaneous injuries.

It is also highly desirable to provide a new needle receptacle capable of use with standard bloodpack needle assemblies of all manufacturers and models.

It is also highly desirable to provide a new needle receptacle that does not have plastic interlocking tabs and protruding members that add to manufacturing costs and which may break due to stress forces.

It is finally highly desirable to provide a new needle receptacle that meets all of the above desired features.

SUMMARY

Therefore, it is an object of the invention to provide a new needle receptacle for use with needle assemblies of the type used by blood banks.

It is also an object of the invention to provide a new needle receptacle that will reduce the number of needle sticks and percutaneous injuries.

It is also an object of the invention to provide a new needle receptacle capable of use with standard bloodpack needle assemblies of all manufacturers and models.

It is also an object of the invention to provide a new needle receptacle that does not have plastic interlocking tabs and protruding members that add to manufacturing costs and which may break due to stress forces.

It is finally an object of the invention to provide a new needle receptacle that meets all of the above desired features.

In the broader aspects of the invention, there is provided a needle receptacle for use with a needle assembly that has a needle mount with a forward end and a rearward end, a needle extending from the forward end of the needle mount and a flexible tube extending from the rearward end of the needle mount. The receptacle includes an elongated hollow body that has a front end and a rear end. The front end is open and sufficiently sized to permit the needle mount to pass axially through it. The rear end has a bore formed in it. The bore is sufficiently sized to permit the tube to pass axially through it. There is also an opening formed in the body between the front end and the rear end for receiving the needle mount and the needle so that the hollow body can be threaded with the needle assembly by way of the opening.

DRAWINGS

The above-mentioned and other features and objects of the invention and the manner of attaining them will become more apparent and the invention itself will be better understood by reference to the following description of an embodiment of the invention taken in conjunction with the accompanying drawings wherein:

FIG. 1 is a perspective view of a standard bloodpack needle assembly fitted with the needle receptacle of the invention.

FIG. 2a is a diagrammatic elevation showing the needle just after insertion into the vein of a donor, the receptacle being in the first position relative to the needle assembly.

FIG. 2b is a similar view to that of FIG. 2a, showing the needle assembly just after a blood withdraw procedure, the receptacle being between the first and second positions relative to the needle assembly.

FIG. 2c is a similar view to that of FIGS. 2a and 2b, showing the needle assembly fully shielded in the receptacle and secured in the second position.

FIG. 3 is a perspective view of the needle receptacle.

FIG. 4 is a plan view of the rear end of the needle receptacle.

FIG. 5 is a side plan view of the needle receptacle showing the opening formed in the body.

DESCRIPTION

Referring to FIG. 1, the needle or catheter assemblies of the type concerned here have needle mount 20 with a forward end 22 and a rearward end 24. A needle 30 extends from forward end 22 of needle mount 20 and a flexible tube 40 extends from the rearward end 24 connecting assembly 100 in fluid-flow connection with a blood collection bag (not shown).

With reference to FIGS. 1 and 3 through 5, needle receptacle 100 comprises a hollow body 110 that is of generally tubular form and is molded from plastics material. Hollow body 110 has an open front end 112 and a closed rear end 114. Rear end 114 has a central bore 115 formed therein, and the open front end 112 has a flared lip 116. An opening 120 is formed in the side of hollow body 110 between the front end 112 and the rear end 114. Opening 120 is sufficiently sized to receive needle 30 and needle mount 20. The interior diameter of bore 115 is slightly larger than the outer diameter of tube 40 so that tube 40 can pass axially through bore 115.

Cutout 117 extends longitudinally and joins opening 120 and central bore 115. Cutout 117 is sufficiently sized to permit flexible tube 40 (when compressed slightly) to pass transaxially therethrough. On the side of body 110 opposite of opening 120, extending longitudinally forward from central bore 115 is tapered slot 118. Slot 118 is configured so that its shape is tapered from rear end 114 toward front end 112, which grasps, or pinches flexible tube 40.

In an embodiment needle receptacle 100 is molded from plastics material and threaded onto tube 40 before (or after) the tube is connected to the blood collection, or IV bag (not shown). Receptacle 100 is formed by die cast or other known plastics manufacturing method. Receptacle 100 preferably has some resiliency so that it is not brittle; and thus, plastics material that possesses such physical and mechanical properties during and after manufacture are preferred. This reduces the likelihood of breakage and permits cutout 117 to expand slightly allowing tube 40 to pass transaxially therethrough.

Since receptacle 100 is defined by single hollow body 110 and has no plastic interlocking tabs or protrusions, receptacle 100 is less expensive to manufacture, especially by die cast techniques.

Needle mount 20 and needle 30 are inserted laterally into opening 120 obliquely relative to the longitudinal axis of receptacle 100. Needle assembly 10 is "fed" forwardly through the open front end 112. Tube 40 is "crimped" between the thumb and forefinger of the user and forced to pass transaxially through cutout 117 and thus, receptacle 100 is "threaded" onto tubing 40, as shown in FIG. 1, in the first position, wherein body 110 is fully clear of needle mount 20 and needle 30.

The manner of using needle receptacle 100 is illustrated in FIGS. 2a–2c. First, with hollow body 110 placed clear of needle mount 20 (FIG. 2a), mount 20 is grasped in the usual manner by the blood technician, or user, and used to insert needle 30 into the vein 37 of the donor's arm 35. After sufficient blood has been collected, the user holds body 110 with one hand and places a swab 38 over the puncture site and holds it and the front portion of body 110 near flared lip 116 against the donor's arm 35 with the thumb and index finger of one hand, as shown in FIG. 2b.

The grasping means for grasping flexible tube 40 and securing body 110 from movement along tube 40 is shown in FIGS. 2c and 3–5. While holding swab 38 and receptacle 100 immobile in this fashion, the user pulls on tube 40 with the other hand (FIG. 2b) in the direction of the arrow withdrawing needle 30 from vein 37 until needle mount 20 and needle 30 are fully shielded by hollow body 110. Flared lip 116 at open front end 112 receives needle assemblies of all manufacturers and models. With reference to FIG. 2c, the user pulls tube 40 upwardly in the direction of the arrow into tapered slot 118 so that body 110 is stayed so that needle mount 20 and needle 30 are fully shielded by hollow body 110.

With needle 30 safely secured inside body 110, the donor is left pressing swab 38 against the puncture site while the user strips tubing 40 of blood, severs or ties tube 40 and disposes of receptacle 100 containing needle assembly 10 without fear of needle stick injury.

Since receptacle 100 is defined by single hollow body 110 and has no plastic interlocking tabs or protrusions, receptacle 100 is less expensive to manufacture, especially by die cast techniques.

While a specific embodiment of the invention has been shown and described herein for purposes of illustration, the protection afforded by any patent which may issue upon this application is not strictly limited to the disclosed embodiment, but extends to all structures and arrangements which fall fairly within the scope of the claims which are appended hereto.

What is claimed is:

1. A needle receptacle for use with a needle assembly that has a needle mount with a forward end and a rearward end, a needle extending from the forward end of the needle mount and a flexible tube extending from the rearward end of the needle mount, the receptacle comprising:
    an elongated hollow body having a front end and a rear end, said front end being open and sufficiently sized to permit the needle mount to pass axially therethrough, said rear end having a bore formed therein sufficiently sized to permit the tube to pass axially therethrough; and
    an opening formed in said body between the front end and said rear end for receiving said needle mount and said needle so that the hollow body can be threaded with the needle assembly via said opening and said front open end.

2. The receptacle of claim 1 wherein said body includes grasping means for grasping the flexible tube so that said body cannot move on the flexible tube toward and away from the needle mount, whereby said body can be stayed in the first position, the second position or therebetween.

3. The receptacle of claim 2 wherein a cutout joining said opening and said bore is formed in said body.

4. The receptacle of claim 3 wherein said front end has a flared lip.

5. The receptacle of claim 4 wherein said grasping means comprises a tapered slot formed in the rear end of the body.

6. The receptacle of claim 1 wherein a cutout joining said opening and said bore is formed in said body.

7. In combination:
    a needle assembly including a needle mount with a forward end and a rearward end, a needle extending from the forward end of the needle mount and a flexible tube extending from the rearward end of the needle mount;
    an elongated hollow body threadedly mounted onto said needle assembly for forward and rearward movement along an axis on said assembly, said hollow body having a front end and a rear end, said front end being open and sufficiently sized to permit the needle mount to pass axially therethrough, said rear end having a bore formed therein sufficiently sized to permit the tube to pass axially therethrough; and
    an opening formed in said body between the front end and said rear end for receiving said needle mount and said needle.

8. The combination of claim 7 wherein a cutout is formed in said body joining said opening and said bore.

9. The receptacle of claim 8 wherein said front end has a flared lip.

10. The receptacle of claim 9 wherein a tapered slot is formed in the rear end of the body.

11. A needle receptacle for use with a needle assembly that has a needle mount with a forward end and a rearward end, a needle extending from the forward end of the needle mount and a flexible tube extending from the rearward end of the needle mount, the receptacle comprising:

a hollow body adapted for slidable mounting on the flexible tubing of a needle assembly for movement toward and away from the needle mount of the assembly, whereby said body can be located in a first position wherein said body is fully clear of the needle mount and the needle, and a second position, wherein said body receives said needle mount so that said needle mount and said needle are fully shielded by said body, wherein said body has an open front end and a rear end, a bore extending through the rear end, and an opening formed in said body between the front end and said rear end.

12. A needle receptacle for use with a needle assembly that has a needle mount with a forward end and a rearward end, a needle extending from the forward end of the needle mount and a flexible tube extending from the rearward end of the needle mount, the receptacle comprising:

a hollow body adapted for slidable mounting on the flexible tubing of a needle assembly for movement toward and away from the needle mount of the assembly, whereby said body can be located in a first position wherein said body is fully clear of the needle mount and the needle, and a second position, wherein said body receives said needle mount so that said needle mount and said needle are fully shielded by said body, wherein said body further comprises grasping means for grasping the flexible tube so that said body cannot move on the flexible tubing toward and away from the needle mount, wherein said body can be stayed in the first position, the second position or therebetween, and wherein said body has an open front end and a rear end, a bore extending through the rear end, and an opening formed in said body between the front end and said rear end.

13. In combination:

a needle assembly including a needle mount with a forward end and a rearward end, a needle extending from the forward end of the needle mount and a flexible tube extending from the rearward end of the needle mount; and a needle receptacle comprising a hollow body adapted for slidable mounting on the flexible tubing of said needle assembly for movement toward and away from the needle mount of the assembly, whereby said body can be located in a first position wherein said body is fully clear of the needle mount and the needle, and a second position, wherein said body receives said needle mount so that said needle mount and said needle are fully shielded by said body, wherein said body has an open front end and a rear end, a bore extending through said rear end and an opening sufficiently sized for receiving said needle mount and said needle formed in said body between the forward end and said rear end.

14. In combination:

a needle assembly including a needle mount with a forward end and a rearward end, a needle extending from the forward end of the needle mount and a flexible tube extending from the rearward end of the needle mount; and a needle receptacle comprising a hollow body adapted for slidable mounting on the flexible tubing of said needle assembly for movement toward and away from the needle mount of the assembly, whereby said body can be located in a first position wherein said body is fully clear of the needle mount and the needle, and a second position, wherein said body receives said needle mount so that said needle mount and said needle are fully shielded by said body, wherein said body includes grasping means for grasping the flexible tube so that said body cannot move on the flexible tube toward and away from the needle mount, whereby said body can be stayed in the first position, the second position or therebetween, wherein said body has an open front end and a rear end, a bore extending through said rear end and an opening sufficiently sized for receiving said needle mount and said needle formed in said body between the forward end and said rear end.

\* \* \* \* \*